(12) United States Patent
Hummel et al.

(10) Patent No.: US 11,028,035 B2
(45) Date of Patent: Jun. 8, 2021

(54) METHOD AND DEVICE FOR PURIFYING ACETONE/WATER MIXTURES BY MEANS OF DOUBLE-EFFECT DISTILLATION

(71) Applicant: Rhodia Acetow GmbH, Freiburg (DE)

(72) Inventors: Andreas Hummel, Freiburg (DE); Thomas Krumrey, Teningen (DE)

(73) Assignee: Rhodia Acetow GmbH, Feiburg (DE)

( * ) Notice: Subject to any disclaimer, the term of this patent is extended or adjusted under 35 U.S.C. 154(b) by 0 days.

(21) Appl. No.: 16/616,163

(22) PCT Filed: Apr. 26, 2018

(86) PCT No.: PCT/EP2018/060734
§ 371 (c)(1),
(2) Date: Nov. 22, 2019

(87) PCT Pub. No.: WO2018/219560
PCT Pub. Date: Dec. 6, 2018

(65) Prior Publication Data
US 2020/0140362 A1    May 7, 2020

(30) Foreign Application Priority Data
May 31, 2017 (EP) .................................... 17173746

(51) Int. Cl.
*C07C 45/82* (2006.01)
*B01D 3/14* (2006.01)
(Continued)

(52) U.S. Cl.
CPC .............. *C07C 45/82* (2013.01); *B01D 3/007* (2013.01); *B01D 3/146* (2013.01); *C07C 49/08* (2013.01)

(58) Field of Classification Search
CPC ........ B01D 3/007; B01D 3/146; C07C 45/82; C07C 49/08
See application file for complete search history.

(56) References Cited

U.S. PATENT DOCUMENTS 4,306,942 A * 12/1981 Brush .................... B01D 3/146
                                                  203/19
4,372,822 A *  2/1983 Muller ................... B01D 3/146
                                                  203/19
(Continued)

FOREIGN PATENT DOCUMENTS

CN       201 701 768 U      1/2011
DE         19940008 A1      3/2001
(Continued)

OTHER PUBLICATIONS

International Search Report and Written Opinion for International Application No. PCT/EP2018/060734 dated Jun. 18, 2018.
(Continued)

*Primary Examiner* — Jonathan Miller
(74) *Attorney, Agent, or Firm* — Greenberg Traurig, LLP

(57) ABSTRACT

The invention relates to a method for separating acetone from acetone/water mixtures, according to which a partial flow of the acetone/water mixture is concentrated in a column operating under positive pressure in order to obtain a product with an acetone concentration of at least 80 wt. %, and a partial flow of the acetone/water mixture is concentrated in a column operating under normal pressure. The top product from the column operated under positive pressure is used to heat the bottom product of the column operated under normal pressure, by means of a heat exchanger, and the top product is then introduced into the column operated under normal pressure, above the supply of the partial flow of the acetone/water mixture. This method allows the specific energy demand for acetone separation to be significantly reduced, thereby presenting considerable cost advantages. The invention also relates to a device for carrying out such a method.

14 Claims, 2 Drawing Sheets

Figure 1:
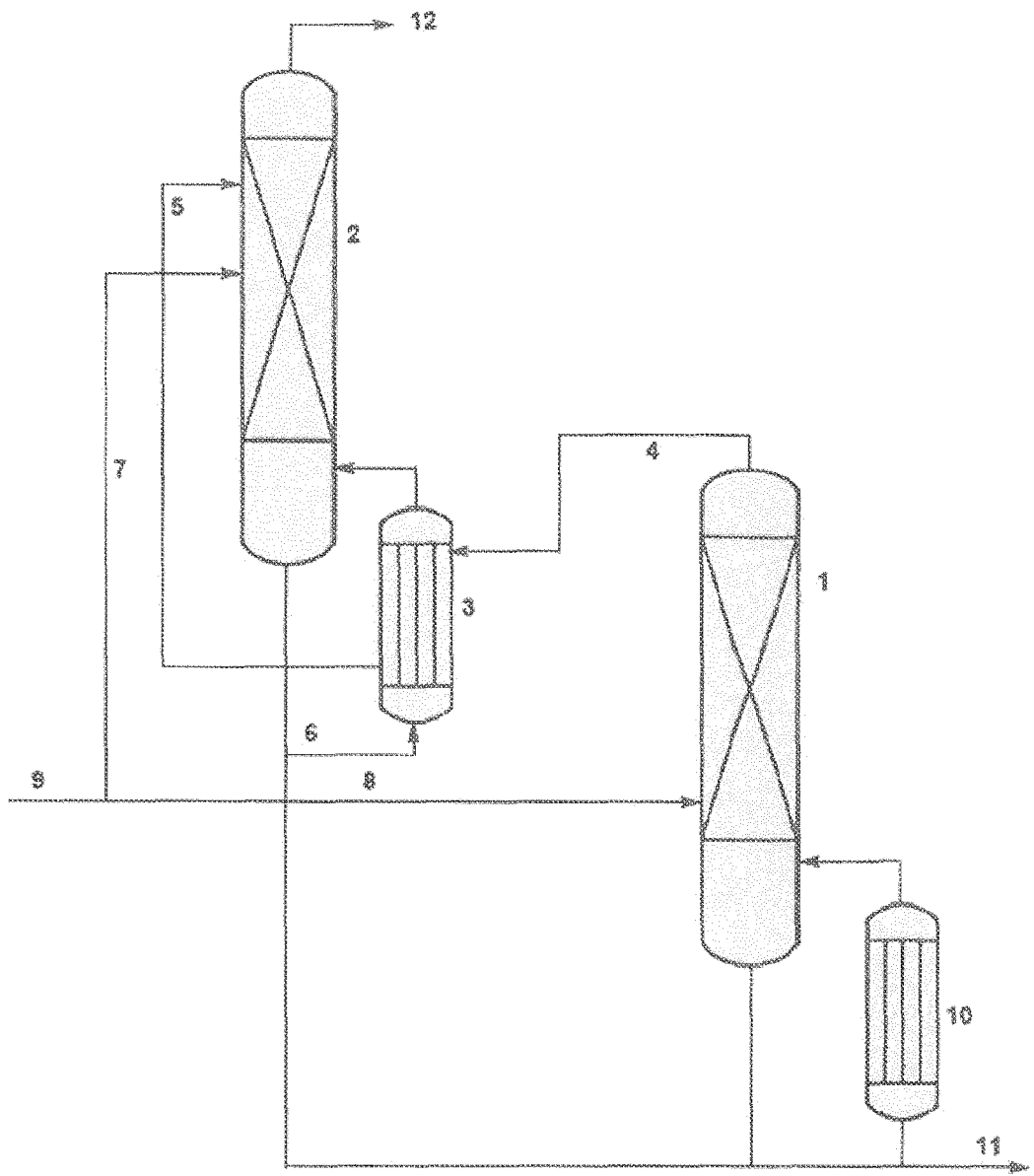

(51) Int. Cl.
*B01D 3/00* (2006.01)
*C07C 49/08* (2006.01)

(56) References Cited

U.S. PATENT DOCUMENTS

| | | | | |
|---|---|---|---|---|
| 4,961,826 A | * | 10/1990 | Grethlein | B01D 3/146 |
| | | | | 203/19 |
| 5,035,776 A | * | 7/1991 | Knapp | C07C 29/84 |
| | | | | 203/19 |
| 9,138,678 B2 | * | 9/2015 | Huang | B01D 71/44 |
| 2017/0203230 A1 | * | 7/2017 | Raiser | B01D 3/007 |

FOREIGN PATENT DOCUMENTS

| | | |
|---|---|---|
| EP | 0767160 B1 | 4/1999 |
| FR | 2 549 043 A1 | 1/1985 |
| JP | H9-124539 A | 5/1997 |
| JP | 2001-81058 A | 3/2001 |
| RU | 2400469 C2 | 9/2010 |

OTHER PUBLICATIONS

Diaz et al., "Techno-economic analysis of extraction-based separation systems for acetone, butanol, and ethanol recovery and purification", Bioresources and Bioprocessing, (2017) 4:12.

You et al., "Reducing process cost and CO2 emissions for extractive distillation by double-effect heat integration and mechanical heat pump", Applied Energy, 166 (2016) 128-140.

Kim, "Energy saving and thermodynamic efficiency of a double-effect distillation column using internal heat integration", Korean J. Chem. Eng., 29 (12), 1680-1687 (2012).

* cited by examiner

METHOD AND DEVICE FOR PURIFYING ACETONE/WATER MIXTURES BY MEANS OF DOUBLE-EFFECT DISTILLATION

RELATED APPLICATIONS

This application is a national phase filing under 35 USC 371 of International Application No. PCT/EP2018/060734, filed on Apr. 26, 2018, which claims the priority of European Patent Application No. 17173746.3, filed on May 31, 2017, the entire contents of which are hereby incorporated by reference.

The present invention relates to a method for separating acetone from acetone/water mixtures using the DED (double-effect distillation) technique in which two rectification columns are operated at different pressures so that the waste heat of the top product of a column operated under pressure can be used to heat the bottom product of a column operated under lower pressure. The present invention further relates to a device for carrying out such a method.

The so-called DED (double-effect distillation) technique has long been known with respect to saving energy in distillation systems. In this technique, two (or more) systems are operated at different pressures, whereby different boiling points result in the top and bottom of the respective columns. Suitably coordinating the pressures can establish cogeneration between these columns so that the top product of a column operated at a higher pressure can heat the bottom of a column operated at a lower pressure. This measure correspondingly conserves heat energy.

However, acetone recovery entails the problem of the boiling points of the top and bottom product being relatively far apart (55° C. to 102° C. at normal pressure), particularly in acetone/water mixtures. As a consequence, a "vacuum tower" in a DED system needs to be operated under a vacuum until the bottom temperature is at least 5 Kelvin below the top temperature of 55° C. of a normal pressure column. This is achieved at approximately 80 mbar absolute but is associated with the considerable disadvantage that because of the low vacuum, the required columns need to be very large in size, which is associated with high capital costs. Moreover, condensation at the top occurs at approximately 0° C. in these vacuum columns making it no longer possible to use inexpensive coolants such as, for example, cooling tower water or respectively air cooling. Nor is influent thermal recovery possible any more.

An alternative variant of double-effect distillation involves coupling a normal pressure column to a pressure column. Pressure here needs to be raised to at least 5 bar absolute in order to enable the thermal coupling as described above. Yet at these pressures, an azeotrope of water and acetone forms such that the purity of the acetone obtained from the pressure column is significantly less than the purity of the acetone obtained from the normal pressure column. Moreover, the risk of acetone byproducts forming, such as in particular diacetone alcohol and mesityl oxide, increases at higher temperatures.

Performing such a process has to date been proposed for purifying aqueous solutions of butanol and acetone, e.g. in the FR 2549043, whereby the organic components of butanol and acetone are enriched to a level of about 60% in a first stage while the acetone and butanol are completely separated from each other in a second stage. The FR 2549043 indicates that the first distillation stage can be configured with two distillation columns, whereby a first distillation column is operated at an increased pressure of from 3 to 10 bar absolute and a second distillation column operated at a pressure of from 0.5 to 1.5 bar absolute. However, since this process does not yield sufficiently pure acetone as the final product in the first stage (the water content after the first stage amounts to approximately 40%; pure acetone is not generated until the second distillation stage), the process of FR 2549043 is associated with the disadvantage of requiring a further distillation stage in order to achieve the necessary purity.

Combining both alternatives could represent a compromise, whereby a column under a slight vacuum is combined with a pressure column operated under a slight overpressure. In existing installations already comprising normal pressure columns, however, this combination is associated with considerably higher capital costs versus the combination of a normal pressure column and a pressure column or, respectively, a low-pressure column and a normal pressure column.

In the context of this prior art, there is a need to provide an energy-efficient method for purifying and separating acetone from acetone/water mixtures which is able to largely eliminate the above-described disadvantages and realize the lowest possible specific energy requirement. The present invention addresses this need.

According to a first aspect, the present invention therefore relates to a method for separating acetone from acetone/water mixtures, comprising
concentrating a partial flow of the acetone/water mixture in at least one column operated under positive pressure, wherein a product having an acetone concentration of at least 80 wt % is obtained,
concentrating a partial flow of the acetone/water mixture in at least one column operated under normal pressure, wherein the top product from the column operated under positive pressure is used to heat the bottom product of the column operated under normal pressure via a heat exchanger, and wherein the top product is subsequently introduced into the column operated under normal pressure above the supply of the partial flow of the acetone/water mixture.

Consequently, the inventive method essentially corresponds to a conventional distillation process using the double-effect distillation technique which accepts that acetone and water cannot be optimally separated within the scope of concentrating a partial flow of the acetone/water mixture in a column operated under positive pressure. This disadvantage is however offset by the fact that the essentially enriched acetone/water mixture, at least with respect to the acetone, is introduced into the concentration column operated at normal pressure so that full separation is possible there. Particularly with respect to acetone-low concentrations of acetone/water mixtures, this processing has the advantage of only a small volume of an already relatively strongly concentrated acetone being introduced into the column operated at normal pressure as the top product of the column operated under pressure. The heat exchanger largely or virtually entirely recycles the energy used in the pressure column. The supply of the acetone-enriched acetone/water mixture also has the effect of being able to sharply reduce the reflux ratio in the column operated at normal pressure, which further reduces the overall energy requirement of the system as a whole. Also of advantage is an only insignificant change in the hydraulic load on the part of the column into which the acetone mixture is fed.

When the foregoing refers to "above" or "below" with respect to the columns, "above" in this context means the part of the column operated at a lower temperature, which is at the "top" relative to the column, and "below" designates the part of the column operated at higher temperature.

Accordingly, the bottom product is obtained within the lower region of the column and the top product within the upper region of the column.

In the context of the present invention, "normal pressure" is to be understood as a pressure ranging from 0.5 to 1.5 and preferentially 0.8 to 1.2 bar absolute.

The column operated under positive pressure is usually operated at a pressure in the range of 4 to 11 bar absolute in the context of the present invention, whereby, however, a positive pressure in the range of 4.5 to 8 bar absolute and in particular 5 to 7 bar absolute can be specified as preferential. Approximately 6 bar absolute is the most preferred pressure for the column operated under positive pressure in the context of the present invention.

To be understood by "acetone/water mixture" in the context of the present invention is a mixture consisting of acetone and water; this is furthermore also to be understood as a mixture consisting substantially of acetone and water. "Substantially" in this regard means a mixture consisting of at least 95% acetone and water by weight, preferentially 97 to 99.9% acetone and water by weight. Further constituents which may be contained in the water/acetone mixture at up to 5% by weight are, for example, hydrocarbons, e.g. so-called spinning oils used during the production of cellulose acetate fibers, diacetone alcohol or mesityl oxide. The acetone/water mixture from which acetone is separated in the method of the present invention preferably comes from a spinning process for producing cellulose acetate fibers as described for example in P. Rustemeyer, Macromol Symp, 2004, 208, 267-291.

Further advantageous in the context of the present invention is for a top product to be obtained in the column operated under positive pressure which has an acetone concentration of at least 90 wt %, preferentially 90 to 99.9 wt %, more preferably 93 to 98 wt %, and further preferably 94 to 96 wt %.

Expedient in the context of the described method is using the waste heat from the bottom product to preheat the acetone/water mixture supplied during the process to the column operated under positive pressure. Particularly expedient is using the bottom product obtained from the column operated under positive pressure to preheat the acetone/water mixture introduced into the column. Appropriately using the waste heat can be realized with the help of a heat exchanger with which the waste heat from the bottom product can be released to the acetone/water mixture supplied to the column.

The columns operated at positive and normal pressure are advantageously to be configured in the context of the described method so as to ensure sufficient separating of acetone and water.

It thereby preferential for the column operated under positive pressure to exhibit 30 to 60 and preferentially 40 to 50 theoretical plates.

For the column operated under normal pressure, a count of 20 to 40 and preferentially 25 to 35 theoretical plates is considered appropriate.

The temperature in the bottom product of the column operated at positive pressure preferably amounts to 130 to 180° C., in particular 150 to 170° C., and most preferentially to about 160° C. in the context of the method indicated herein. The suitable temperature of the top product of this column is approximately 100 to 130° C. and in particular approximately 105 to 120° C. In order to ensure a sufficiently effective transfer of heat to the bottom product of the column operated under normal pressure, the temperature of the top product should furthermore preferably be at least 5° C. and in particular at least 10° C. higher than the temperature of the bottom product in the column operating under normal pressure.

According to the invention, the method is advantageously to be configured such that acetone is concentrated to a concentration of at least 98 wt %, particularly preferentially to at least 98.5 wt %, and further preferentially to at least 98.5 to 99.9 wt % in the at least one column operated under normal pressure. Alternatively or additionally thereto, it is expedient for the column operating under normal pressure to be operated at a reflux ratio in the range of 2 to 5 and preferentially 3 to 4.

The top product obtained from the column operated at normal pressure is advantageously condensed in a cooler within the scope of the inventive method so as to obtain liquid acetone. Regular cooling water is preferably used for this purpose.

The design to the inventive method, entailing thermally coupling the at least one column operated at positive pressure and the at least one column operated at normal pressure, enables considerable energy savings.

The specific energy consumption of the inventive method can be reduced even further if a third column operating under a vacuum is provided. In this embodiment of the invention, the inventive method is to be configured such that in addition to the above-cited steps, it further includes:

concentrating a partial flow of the acetone/water mixture in at least one column operating under a vacuum, wherein the top product from the column operated under normal pressure is used to heat the bottom product of the column operated under a vacuum via a heat exchanger.

"Vacuum" in the context of the present invention is to be understood as a pressure in the range of <0.5, in particular 0.05 to <0.5 bar absolute.

By providing a third column, this embodiment of the invention entails an increase in capital costs but in return even further lowers the energy costs of ongoing operation.

Additionally, in this embodiment of the invention in which at least three columns are provided, the method can be configured such that the bottom product from the column operated under normal pressure can be introduced into the column operated under vacuum below the supply of the partial flow of the acetone/water mixture.

This embodiment has the additional advantage of achieving even greater acetone depletion in the bottom product of the column operated at normal pressure. This is advantageous with respect to environmental protection aspects and thus also economic aspects.

A further aspect of the present invention relates to a device for realizing a method as described above, wherein the device comprises the following:

at least one column 1 for separating a partial flow of an acetone/water mixture which is designed to be operated under positive pressure, at least one column 2 for separating a partial flow of an acetone/water mixture which is designed to be operated under normal pressure, supply lines for partial flows 7, 8 of an acetone/water mixture to the separation columns, at least one heat exchanger 3 in fluid communication with the top of the column 1 designed for operation at positive pressure and the bottom of the column 2 designed for operation at normal pressure so as to enable a transfer of heat between the top product of the column 1 designed for operation at positive pressure and the bottom product of column 2 designed for operation at normal pressure, a supply line 5 for the top product of column 1 designed for operation at positive pressure via which the heat exchanger 3 is connected to the upper part of column 2 designed for operation at normal pressure.

Supply line 5 is advantageously fit to column 2 designed for operation at normal pressure above the supply line 7 of a partial flow of acetone/water mixture to column 2.

In one embodiment, the method is designed so as to provide a collecting device for the top product in the area of supply line 5, in which it is expanded to the pressure prevailing in column 2 before being fed into same. The collecting device, e.g. in the form of a tank or equivalent reservoir, is positioned in this embodiment in the area of the supply line 5 between the heat exchanger 3 and column 2.

Moreover preferential is for the described device to comprise a condensation device for the top product generated in the column designed to operate under normal pressure.

Lastly, it is preferential for the inventive device to comprise a heat exchanger 10 in fluid communication with the bottom product of column 1 designed for operation under positive pressure and the supply line 8 for the partial flow of an acetone/water mixture to said column.

The present invention will be explained in greater detail in the following with reference to the figures.

FIG. 1 shows an inventive device in which one column 1, designed for operation at positive pressure, and one column 2, designed for operation at normal pressure, are connected together. The top product, which preferably has an acetone concentration of at least 90 wt %, preferentially 90 to 99.9 wt %, more preferably 93 to 98 wt %, and further preferably 94 to 96 wt %, is conveyed into a heat exchanger 3 via discharge line 4 and from there introduced into column 2 via supply line 5. Acetone/water mixture is introduced into columns 1 and 2 via the sub-lines 7 and 8 from a common supply line 9. The heat exchanger 3 is likewise connected to the bottom product of column 2 in circulation 6 in order to enable an exchange of heat via the output of waste heat from the top product of column 1 to the bottom product of the column 2. Substantially pure acetone is obtained as top product from column 2 via discharge line 12. To be understood as substantially pure acetone within the meaning of the present application is preferably a product having an acetone content of at least 98 wt %, preferentially at least 98.5 wt %, in particular 98.5 to 99.9 wt %. The bottom product generated in separation column 1 is likewise integrated into a circulation with a heat exchanger 10 in that additional heat is able to be supplied to the bottom product, for example via steam accordingly heated to a high temperature. Excess bottom product is removed from the inventive device as waste water via discharge line 11. The waste water line 11 is moreover connected to the bottom product circulation 6 of column 2 in order to purge its resultant excess bottom product.

According to the calculations employed, the methodology and device of the present invention can significantly reduce the specific energy requirement by about 35 to 45%. Compared to the theoretical alternatives described above, the volume of capital expenditure likewise decreases considerably as only one new column is required and, where applicable, existing normal pressure columns may be able to be integrated without major change.

One embodiment of the inventive device provides for a third column designed for operation under vacuum. In this embodiment, the inventive device comprises the following:

at least one column 1 for separating a partial flow of an acetone/water mixture which is designed to be operated under positive pressure, at least one column 2a for separating a partial flow of an acetone/water mixture which is designed to be operated under normal pressure, at least one column 2b for separating a partial flow of an acetone/water mixture which is designed to be operated under a vacuum, supply lines for partial flows 7a, 7b, 8 of an acetone/water mixture to the separation columns, at least one heat exchanger 3a in fluid communication with the top of the column 1 designed for operation at positive pressure and the bottom of the column 2a designed for operation at normal pressure so as to enable a transfer of heat between the top product of the column 1 designed for operation at positive pressure and the bottom product of column 2 designed for operation at normal pressure, at least one heat exchanger 3b in fluid communication with the top of the column 2a designed for operation at normal pressure and the bottom of the column 2b designed for operation under a vacuum so as to enable a transfer of heat between the top product of the column 2a designed for operation at normal pressure and the bottom product of column 2b designed for operation under vacuum, a supply line 5 for the top product of column 1 designed for operation at positive pressure via which the heat exchanger 3a is connected to the upper part of column 2a designed for operation at normal pressure.

Supply line 5 is advantageously fit to column 2a above the supply line 7a of a partial flow of acetone/water mixture to column 2a designed for operation at normal pressure.

Figure 2:
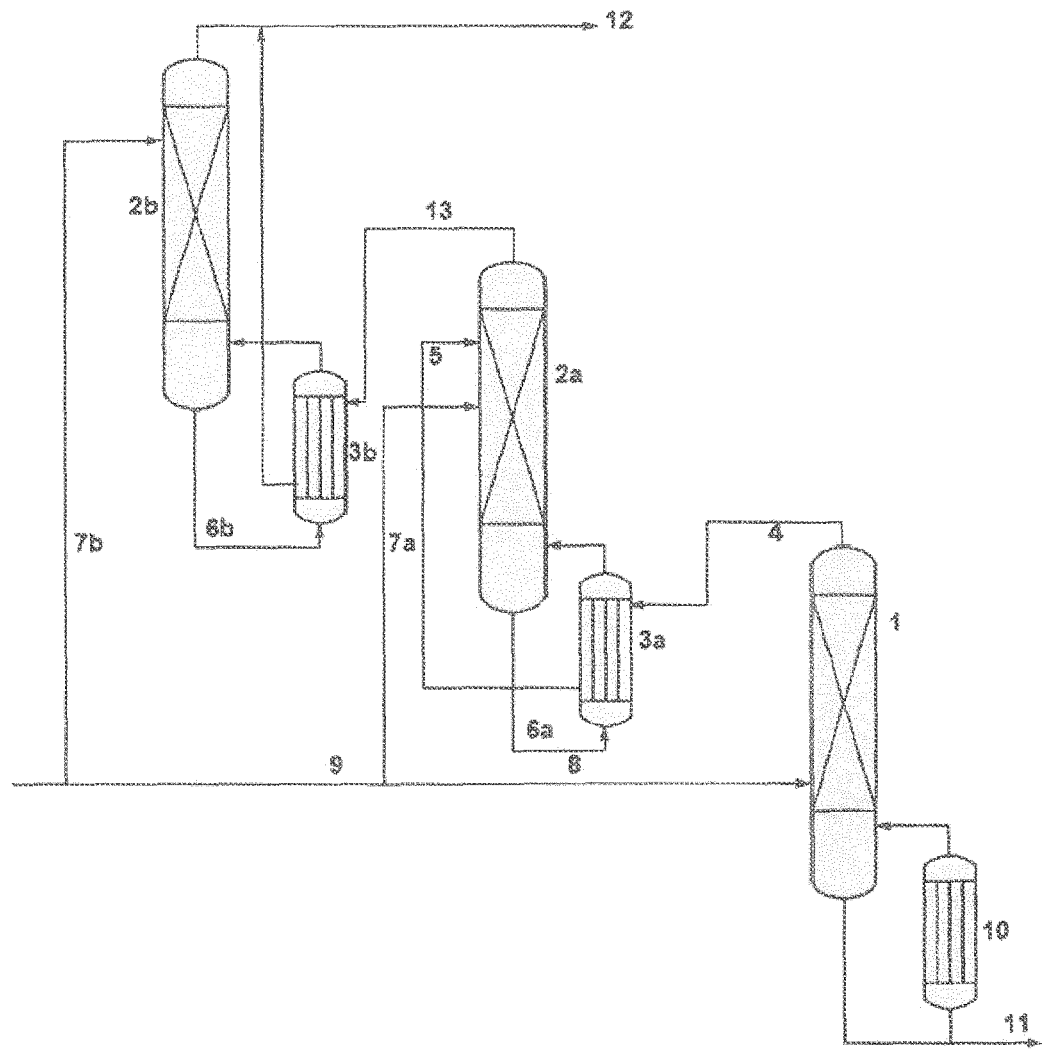

This embodiment of the inventive device is shown in FIG. 2.

A further supply line can additionally be provided in this embodiment of the invention via which the bottom product of column 2a operated at normal pressure can be introduced into column 2b operated under vacuum below the supply of the partial flow of the acetone/water mixture. This additional feature enables even greater acetone depletion in the bottom product of column 2a.

LIST OF REFERENCE NUMERALS

1 column for operation at positive pressure
2, 2a, 2b column for operation at normal pressure
3, 3a, 3b heat exchanger
4, 4a, 4b top product supply line to heat exchanger
top product supply line in column 2
6, 6a, 6b bottom product circulation
7, 7a, 7b partial flow supply line to column 2
8 partial flow supply line to column 1
9 main line for acetone/water mixture
10 heat exchanger
11 waste water discharge line
12 acetone discharge line
13 tank
14a, 14b top product supply line in columns 2a and 2b
15 return line to column 1
16 condensation device
17 condensation device

The invention claimed is:

1. A method for separating acetone from an acetone/water mixture, comprising:
concentrating a partial first flow of the acetone/water mixture in at least one first column to produce a product having an acetone concentration of at least 80 wt %,
wherein the at least one first column is operated under positive pressure;
concentrating a partial second flow of the acetone/water mixture in at least one second column,
wherein the at least one second column is operated under normal pressure,
wherein a top product from the at least one first column is used to heat a bottom product of the at least one second column via a heat exchanger, and
wherein the top product is subsequently introduced into the at least one second column above a supply of the partial second flow of the acetone/water mixture.

2. The method according to claim 1, wherein the at least one first column is operated at a positive pressure in the range of 4.5 to 8 bar absolute.

3. The method according to claim 1 further comprising a top product having an acetone concentration of at least 90 wt % is obtained in the at least one first column.

4. The method according to claim 1, wherein the bottom product obtained from the at least one first column is used to preheat the acetone/water mixture introduced into the at least one second column.

5. The method according to claim 1, wherein the at least one first column exhibits 30-60 theoretical plates.

6. The method according to claim 1, wherein the at least one second column exhibits 20-40 theoretical plates.

7. The method according to claim 1 further comprising:
concentrating a partial third flow of the acetone/water mixture in at least one third column,
wherein the at least one third column is operated under a vacuum,
wherein a top product from the at least one second column is used to heat a bottom product of the at least one third column via a heat exchanger.

8. The method according to claim 7, wherein the bottom product from the at least one second column is introduced into the at least one third column below the supply of the partial third flow of the acetone/water mixture.

9. The method according to claim 1, wherein the acetone in the at least one second column is concentrated to a concentration of at least 98 wt %.

10. The method according to claim 1, wherein the at least one second column is operated at a reflux ratio of from 1 to 2.

11. A device comprising:
at least one first column for separating a partial first flow of an acetone/water mixture,
wherein the at least one first column is operated under positive pressure,
at least one second column for separating a partial second flow of an acetone/water mixture,
wherein the at least one second column is operated under normal pressure,
supply lines for the partial first flow and the partial second flow of an acetone/water mixture to the at least one first column and the at least one second column,
at least one heat exchanger in fluid communication with a top of the at least one first column and a bottom of the at least one second column configured to enable a transfer of heat between a top product of the at least one first column and the bottom product of the at least one second column, and
a supply line for the top product of the at least one first column via which the at least one heat exchanger is connected to an upper part of the at least one second column,
wherein the supply line is connected to the at least one second column above the supply line for a partial second flow of an acetone/water mixture.

12. The device according to claim 11 further comprising a condensation device for the top product generated in the at least one second column.

13. The device according to claim 11 further comprising a heat exchanger in fluid communication with the bottom product of the at least one first column and the supply line for the partial first flow of an acetone/water mixture to said column.

14. The device according to claim 11, wherein the device further comprises:
at least one third column for separating a partial third flow of an acetone/water mixture,
wherein the at least one third column is operated under a vacuum,
a supply line for the partial third flow of the acetone water mixture to the at least one third column,
at least one heat exchanger in fluid communication with the top of the at least one second column and the bottom of the at least one third column configured to enable a transfer of heat between the top product of the at least one second column and the bottom product of the at least one third column.

* * * * *